US007009092B1

(12) United States Patent
Jane et al.

(10) Patent No.: US 7,009,092 B1
(45) Date of Patent: Mar. 7, 2006

(54) TRANSGENIC CORN PLANTS HAVING SEEDS WITH MODIFIED CORNSTARCH CHARACTERISTICS AND METHOD OF MAKING THE TRANSGENIC CORN PLANTS

(75) Inventors: Jay-lin Jane, Ames, IA (US); Beiquan Mou, Salinas, CA (US); Christer Jansson, Vellentuna (SE); Chuanxin Sun, Uppsala (SE)

(73) Assignee: Iowa State University Research Foundation, Ames, IA (US)

( * ) Notice: Subject to any disclaimer, the term of this patent is extended or adjusted under 35 U.S.C. 154(b) by 270 days.

(21) Appl. No.: 10/162,948

(22) Filed: Jun. 4, 2002

Related U.S. Application Data

(60) Provisional application No. 60/295,649, filed on Jun. 4, 2001.

(51) Int. Cl.
C12N 15/29 (2006.01)
C12N 15/82 (2006.01)
A01H 5/00 (2006.01)
A01H 5/10 (2006.01)

(52) U.S. Cl. .................. 800/320.1; 800/284; 800/290; 800/278; 435/468; 435/101; 435/412

(58) Field of Classification Search ................ 800/298, 800/290, 278, 284, 320.1; 435/468, 419, 435/101, 412
See application file for complete search history.

(56) References Cited

U.S. PATENT DOCUMENTS 5,912,413 A    6/1999 Myers et al.

FOREIGN PATENT DOCUMENTS

WO    WO 97/22703    * 6/1997

OTHER PUBLICATIONS

Slattery et al (2000, Trends in Plant Science 5(7):291-298).*
Sun et al (1998, Plant Physiol. 118:37-49).*
Umemoto T, Yano M, Satoh H, Shomura A, and Nakamura Y., "Mapping of a gene responsible for the difference in amylopectin structure between japonica-type and indica-type rice varieties", Theor Appl Genet 104(1):1-8 (Jan. 2002).
Rahman S. Regina A, Li Z, Mukai Y, Yamamoto M, Kosar-Hashemi B, Abrahams S, Morell MK., "Comparison of starch-branching enzyme genes reveals evolutionary relationships among isoforms. Characterization of a gene for starch-branching enzyme IIa from the wheat genome donor *Aegilops tauschii*", Plant Physiol 125(3):1314-24 (Mar. 2001).
Edwards A, Fulton DC, Hylton CM, Jobling SA, Gidley M, Rossner U, Martin C, Smith AM. (1999) A combined reduction in activity of starch synthases II and III of potato has novel effects on the starch of tubers. Plant J 17(3):251-261.
Flipse E, Huisman JG, Vries BJD, Bergervoet JEM, Jacobsen E, Visser RGF. (1994) Expression of a wild-type GBSS gene introduced into an amylose-free potato mutant by *Agrobacterium tumefaciens* and the inheritance of the inserts at the microsporic level. Theor Appl Genet. 88:369-375.
Jane J, Chen Y, Lee L, McPherson A, Wong K, Radosavljevic, Kasemsuwan T. (1999) Effects of amylopectin branch chain length and amylose content on the gelatinization and pasting properties of starch. Cereal Chem. 76(5): 629-637.
Jobling SA, Schwall GP, Westcott RJ, Sidebottom CM, Debet M, Gidley MJ, Jeffcoat R, Safford R. (1999) A minor form of starch branching enzyme in potato (*Solanum tuberosum* L.) tubers has a major effect on starch structure: cloning and characterization of multiple forms of SBE A. Plant J 18(2):163-171.
Kortstee AJ, Vermeesch AMS, Vries BJD, Jacobsen E, Visser RGF (1996) Expression of *Escherichia coli* branching enzyme in tubers of amylose-free transgenic potato leads to an increased branching degree of the amylopectin. Plant J 10(1):83-90.
Lloyd JR, Landschutze V, Kossmann J. (1999) Simultaneous antisense inhibition of two starch-synthase isoforms in potato tubers leads to accumulation of grossly modified amylopectin. Biochem J. 338:515-521.
Martin C, Smith AM. (1995) Starch biosynthesis. Plant Cell. 7:971-985.
Myers AM, Morell MK, James MG, Ball SG. (2000) Recent progress toward understanding biosynthesis of the amylopectin crystal. Plant Physiol. 122: 989-997.
Safford R, Jobling SA, Sidebottom CM, Westcott RJ, Cooke D, Tober KJ, Strongitharm BH, Russell A, Gidley MJ. (1998) Consequences of antisense RNA inhibition of starch branching enzyme activity on properties of potato starch. Carbohydrate Polymers 35: 155-168.

(Continued)

Primary Examiner—David T. Fox
Assistant Examiner—Stuart F. Baum
(74) Attorney, Agent, or Firm—Zhibin Ren; Quarles & Brady, LLP

(57) ABSTRACT

Cornstarch characteristics can be changed by expressing a non-corn plant starch branching enzyme in a corn plant. In a preferred embodiment, transgenic corn plants containing the barley starch branching enzyme IIa transgene was generated. Some transgenic corn plants produced seeds containing cornstarch with lowered gelatinization temperature and retrogradation rate while others produced seeds containing cornstarch with higher retrogradation rate when compared to non-transgenic corn plants.

15 Claims, 2 Drawing Sheets

OTHER PUBLICATIONS

Schwall GP, Safford R, Westcott RJ, Jeffcoat R, Tayal A, Shi YC, Gidley MJ, Jobling SA. (2000) Production of very-high-amylose potato starch by inhibition of SBE A and B. Nat Biotechnol. 18(5):551-554.

SEO B, Kim S, Scott MP, Singletary GW, Wong K, James MG, Myers AM. (2002) Functional interactions between heterologously expressed starch-branching enzymes of maize and the glycogen synthases of brewer's yeast. Plant Physiology 128:1189-1199.

Shi YC, Seib PA. (1992) The structure of four waxy starches related to gelatinization and retrogradation. Carbohydr Res. 227:131-145.

Shi YC, Seib PA. (1995) Fine structure of maize starches from four wx-containing genotypes of the W64A inbred line in relation to gelatinization and retrogradation. Carbohydrate Polymers. 26:141-47.

Smith AM. (2001) The Biosynthesis of Starch Granules. Biomacromolecules 2:335-341.

Song Y, Jane J (2000) Characterization of barley starches of waxy, normal, and high amylose varieties. Carbohydrate Polymers. 41:365-377.

Stark DM, Timmerman KP, Barry GF, Preiss J, Kishore GM. (1992) Regulation of the amount of starch in plant tissues by ADP glucose pyrophosphorylase. Science. 258:287-292.

Sun C, Sathish P, Ahlandsberg S, Jansson C. (1998) The two genes encoding starch-branching enzymes IIa and IIb are differentially expressed in barley. Plant Physiol. 118:37-49.

Terada R, Nakajima M, Isshiki M, Okagaki RJ, Wessler SR, Shimamoto K. (2000) Antisense Waxy genes with highly active promoters effectively suppress Waxy gene expression in transgenic rice. Plant Cell Physiol. 41(7):881-888.

Wolters AA, Visser RG. (2000) Gene silencing in potato: allelic differences and effect of ploidy. Plant Mol Biol. 43:377-386.

Yoo S, Spalding MH, Jane J. (2002) Charterization of cyanobacterial glycogen isolated from the wild type and from a mutant lacking of branching enzyme. Carbohydrate Research 337:2195-2203.

Yuan RC, Thompson DB, Boyer CD. (1993) Fine structure of amylopectin in relation to gelatinization and retrogradation behavior of maize starches from three wx-containing genotypes in two inbred lines. Cereal Chem. 70:81-89.

* cited by examiner

SEQUENCE LISTING

<160> NUMBER OF SEQ ID NOS: 12

<210> SEQ ID NO 1
<211> LENGTH: 2554
<212> TYPE: DNA

<213> ORGANISM: Hordeum vulgare
<220> FEATURE:
<221> NAME/KEY: CDS
<222> LOCATION: (7)..(2208)

<400> SEQUENCE: 1

```
ggcgag atg gcg gaa gta aac atg aca ggg ggg gct gca gaa aaa ctt      48
       Met Ala Glu Val Asn Met Thr Gly Gly Ala Ala Glu Lys Leu
         1               5                  10 gaa tct tca gaa ccg act cag ggt att gcg gaa aca atc act gat ggt      96
Glu Ser Ser Glu Pro Thr Gln Gly Ile Ala Glu Thr Ile Thr Asp Gly
 15                  20                  25                  30 gta acc aaa gga gtt aaa gaa cta gtc gtt ggg gag aaa ccg caa gtt     144
Val Thr Lys Gly Val Lys Glu Leu Val Val Gly Glu Lys Pro Gln Val
                 35                  40                  45 gtc cca aaa cca gga gat ggg caa aaa ata tac gag att gac cca acg     192
Val Pro Lys Pro Gly Asp Gly Gln Lys Ile Tyr Glu Ile Asp Pro Thr
             50                  55                  60 ctg aaa gat ttt cgg agc cat ctt gac tac cga tac agc gaa tac aag     240
Leu Lys Asp Phe Arg Ser His Leu Asp Tyr Arg Tyr Ser Glu Tyr Lys
         65                  70                  75 aga att cgt gct gct att gac caa cat gaa ggt gga ttg gaa gtt ttt     288
Arg Ile Arg Ala Ala Ile Asp Gln His Glu Gly Gly Leu Glu Val Phe
 80                  85                  90 tct cgt ggt tat gaa aag ctt gga ttt acc cgc agt gct aaa ggt atc     336
Ser Arg Gly Tyr Glu Lys Leu Gly Phe Thr Arg Ser Ala Lys Gly Ile
 95                 100                 105                 110 act tac cga gaa tgg gct cct gga gcg cat tct gca gca tta gta ggt     384
Thr Tyr Arg Glu Trp Ala Pro Gly Ala His Ser Ala Ala Leu Val Gly
                115                 120                 125 gac ttc aac aat tgg aac cca aat gca gat act atg acc aga gat gat     432
Asp Phe Asn Asn Trp Asn Pro Asn Ala Asp Thr Met Thr Arg Asp Asp
            130                 135                 140 tat ggt gtt tgg gag att ttc ctc cct aac aat gct gat gga tcc cct     480
Tyr Gly Val Trp Glu Ile Phe Leu Pro Asn Asn Ala Asp Gly Ser Pro
        145                 150                 155 gct att cct cat ggc tca cgt gta aag ata cgg atg gat act cca tct     528
Ala Ile Pro His Gly Ser Arg Val Lys Ile Arg Met Asp Thr Pro Ser
    160                 165                 170 ggt gtg aag gat tca att tct gct tgg atc aag ttc tct gtg cag gct     576
Gly Val Lys Asp Ser Ile Ser Ala Trp Ile Lys Phe Ser Val Gln Ala
175                 180                 185                 190 cca ggt gaa ata cca ttc aat ggc ata tat tat gat cca cct gaa gag     624
Pro Gly Glu Ile Pro Phe Asn Gly Ile Tyr Tyr Asp Pro Pro Glu Glu
                195                 200                 205 gag aag tat gtc ttc caa cat cct caa cct aaa cga cca gag tca cta     672
Glu Lys Tyr Val Phe Gln His Pro Gln Pro Lys Arg Pro Glu Ser Leu
            210                 215                 220 agg ata tat gaa tca cac att gga atg agc agc ccg gaa ccg aag ata     720
Arg Ile Tyr Glu Ser His Ile Gly Met Ser Ser Pro Glu Pro Lys Ile
        225                 230                 235 aat tca tat gct aat ttt agg gat gag gtg ctg cca aga att aaa agg     768
Asn Ser Tyr Ala Asn Phe Arg Asp Glu Val Leu Pro Arg Ile Lys Arg
    240                 245                 250 ctt gga tac aat gca gtg cag ata atg gca atc cag gag cat tca tac     816
Leu Gly Tyr Asn Ala Val Gln Ile Met Ala Ile Gln Glu His Ser Tyr
255                 260                 265                 270 tat gcg agc ttt ggg tac cat gtt act aat ttt ttt gca cca agt agc     864
Tyr Ala Ser Phe Gly Tyr His Val Thr Asn Phe Phe Ala Pro Ser Ser
                275                 280                 285
```

-continued

| | |
|---|---|
| cgt ttt gga act cca gag gac tta aaa tcc ttg atc gat aga gca cat<br>Arg Phe Gly Thr Pro Glu Asp Leu Lys Ser Leu Ile Asp Arg Ala His<br>              290                    295                    300 | 912 |
| gag ctt ggt ttg ctt gtt ctt atg gat att gtt cat agt cat tcg tca<br>Glu Leu Gly Leu Leu Val Leu Met Asp Ile Val His Ser His Ser Ser<br>305                    310                    315 | 960 |
| aat aat acc ctt gac ggt ttg aat ggt ttc gat ggc act gat aca cat<br>Asn Asn Thr Leu Asp Gly Leu Asn Gly Phe Asp Gly Thr Asp Thr His<br>320                    325                    330 | 1008 |
| tac ttc cac ggt ggt cca cgt ggc cat cat tgg atg tgg gat tct cgt<br>Tyr Phe His Gly Gly Pro Arg Gly His His Trp Met Trp Asp Ser Arg<br>335                    340                    345                    350 | 1056 |
| ctg ttc aac tat ggg agt tgg gaa gta tta aga ttc tta ctg tca aac<br>Leu Phe Asn Tyr Gly Ser Trp Glu Val Leu Arg Phe Leu Leu Ser Asn<br>              355                    360                    365 | 1104 |
| gcg aga tgg tgg ctt gaa gaa tat aag ttt gat gga ttt cga ttt gat<br>Ala Arg Trp Trp Leu Glu Glu Tyr Lys Phe Asp Gly Phe Arg Phe Asp<br>              370                    375                    380 | 1152 |
| ggg gtg act tcc atg atg tat act cac cat gga tta caa atg aca ttt<br>Gly Val Thr Ser Met Met Tyr Thr His His Gly Leu Gln Met Thr Phe<br>        385                    390                    395 | 1200 |
| act ggg aac tat ggc gag tat ttt gga ttc gcc act gat gtt gat gcg<br>Thr Gly Asn Tyr Gly Glu Tyr Phe Gly Phe Ala Thr Asp Val Asp Ala<br>400                    405                    410 | 1248 |
| gtg gtt tac tta atg ctg gtc aac gat cta att cat gga ctt tat ccg<br>Val Val Tyr Leu Met Leu Val Asn Asp Leu Ile His Gly Leu Tyr Pro<br>415                    420                    425                    430 | 1296 |
| gat gct gta tcc att ggt gaa gat gtc agc gga atg cct aca ttt tgc<br>Asp Ala Val Ser Ile Gly Glu Asp Val Ser Gly Met Pro Thr Phe Cys<br>              435                    440                    445 | 1344 |
| atc cct gtc cca gat ggt ggt gtt ggt ttt gac tat cgc ctg cat atg<br>Ile Pro Val Pro Asp Gly Gly Val Gly Phe Asp Tyr Arg Leu His Met<br>              450                    455                    460 | 1392 |
| gct gta gca gat aaa tgg att gaa ctc ctc aag caa agt gac gaa tct<br>Ala Val Ala Asp Lys Trp Ile Glu Leu Leu Lys Gln Ser Asp Glu Ser<br>              465                    470                    475 | 1440 |
| tgg aaa atg ggc gat att gtg cac acc cta aca aat aga agg tgg ctt<br>Trp Lys Met Gly Asp Ile Val His Thr Leu Thr Asn Arg Arg Trp Leu<br>480                    485                    490 | 1488 |
| gag aag tgt gtc act tat gca gaa agt cat gat caa gca cta gtt ggt<br>Glu Lys Cys Val Thr Tyr Ala Glu Ser His Asp Gln Ala Leu Val Gly<br>495                    500                    505                    510 | 1536 |
| gac aag act att gca ttc tgg ttg atg gat aag gat atg tat gat ttc<br>Asp Lys Thr Ile Ala Phe Trp Leu Met Asp Lys Asp Met Tyr Asp Phe<br>                    515                    520                    525 | 1584 |
| atg gct ctg gat aga cct tca acc cct cgc att gat cgt ggc ata gca<br>Met Ala Leu Asp Arg Pro Ser Thr Pro Arg Ile Asp Arg Gly Ile Ala<br>              530                    535                    540 | 1632 |
| tta cat aaa atg atc agg ctt gtc acc atg ggt tta ggt ggc gaa ggc<br>Leu His Lys Met Ile Arg Leu Val Thr Met Gly Leu Gly Gly Glu Gly<br>        545                    550                    555 | 1680 |
| tat ctt aat ttc atg gga aat gag ttt ggg cat cct gaa tgg ata gat<br>Tyr Leu Asn Phe Met Gly Asn Glu Phe Gly His Pro Glu Trp Ile Asp<br>560                    565                    570 | 1728 |
| ttt cca aga ggt ccg caa act ctt cca acc ggc aaa gtt ctc cct gga<br>Phe Pro Arg Gly Pro Gln Thr Leu Pro Thr Gly Lys Val Leu Pro Gly<br>575                    580                    585                    590 | 1776 |
| aat aac aat agt tat gat aaa tgc cgc cgt aga ttt gat ctt gga gat<br>Asn Asn Asn Ser Tyr Asp Lys Cys Arg Arg Arg Phe Asp Leu Gly Asp<br>              595                    600                    605 | 1824 |

```
gca gat ttt ctt aga tat cgt ggt atg caa gag ttc gat cag gca atg      1872
Ala Asp Phe Leu Arg Tyr Arg Gly Met Gln Glu Phe Asp Gln Ala Met
            610                 615                 620 cag cat ctt gag gaa aaa tat ggg ttt atg aca tct gag cac cag tat      1920
Gln His Leu Glu Glu Lys Tyr Gly Phe Met Thr Ser Glu His Gln Tyr
            625                 630                 635 gtt tct cgg aaa cat gag gaa gat aag gtg atc atc ttc gaa aga gga      1968
Val Ser Arg Lys His Glu Glu Asp Lys Val Ile Ile Phe Glu Arg Gly
        640                 645                 650 gat ttg gta ttt gtt ttc aac ttc cac tgg agc aat agc aaa aaa gac      2016
Asp Leu Val Phe Val Phe Asn Phe His Trp Ser Asn Ser Lys Lys Asp
655                 660                 665                 670 tac cgt gtt ggg tgt tcc aag cct ggg aag tac aag gtg gcc tta gac      2064
Tyr Arg Val Gly Cys Ser Lys Pro Gly Lys Tyr Lys Val Ala Leu Asp
                675                 680                 685 tct gat gat gca ctc ttt ggt gga ttc agc agg ctt gat cat gat gtc      2112
Ser Asp Asp Ala Leu Phe Gly Gly Phe Ser Arg Leu Asp His Asp Val
            690                 695                 700 gac tac ttc aca acc gaa cat ccg cat gac aac agg cca cgc tct ttc      2160
Asp Tyr Phe Thr Thr Glu His Pro His Asp Asn Arg Pro Arg Ser Phe
        705                 710                 715 tcg gtg tac act ccg agc aga act gcg gtc gtg tat gcc ctt aca gag      2208
Ser Val Tyr Thr Pro Ser Arg Thr Ala Val Val Tyr Ala Leu Thr Glu
    720                 725                 730 taagaaccag cagctgtttg ttacaaggca aaaagagaac tccagtgagc tcgtggattg    2268
tgagcgaagc gacgggcaac ggtccgagac tgttctaacc gccgtgattg ggaggggatc    2328
gtgcctcttc cccagatgct aggaggatca gatggatagg tagcttgctg gcgagccctc    2388
gttttcaagt gacctgcgaa agaaaatgga cgggcctggg tgacattttg tagtgctgca    2448
ctgaaccatc ctatctctca cattcccggt tgtttatgta catataaact aataattgcc    2508
cgtgcgcttc aacttggaca aaaaaaaaaa aaaaaaaaa aaaaa                     2554
```

<210> SEQ ID NO 2
<211> LENGTH: 734
<212> TYPE: PRT
<213> ORGANISM: Hordeum vulgare

<400> SEQUENCE: 2

```
Met Ala Glu Val Asn Met Thr Gly Gly Ala Ala Glu Lys Leu Glu Ser
  1               5                  10                  15

Ser Glu Pro Thr Gln Gly Ile Ala Glu Thr Ile Thr Asp Gly Val Thr
             20                  25                  30

Lys Gly Val Lys Glu Leu Val Gly Glu Lys Pro Gln Val Val Pro
         35                  40                  45

Lys Pro Gly Asp Gly Gln Lys Ile Tyr Glu Ile Asp Pro Thr Leu Lys
     50                  55                  60

Asp Phe Arg Ser His Leu Asp Tyr Arg Tyr Ser Glu Tyr Lys Arg Ile
 65                  70                  75                  80

Arg Ala Ala Ile Asp Gln His Glu Gly Gly Leu Glu Val Phe Ser Arg
                 85                  90                  95

Gly Tyr Glu Lys Leu Gly Phe Thr Arg Ser Ala Lys Gly Ile Thr Tyr
            100                 105                 110

Arg Glu Trp Ala Pro Gly Ala His Ser Ala Ala Leu Val Gly Asp Phe
        115                 120                 125

Asn Asn Trp Asn Pro Asn Ala Asp Thr Met Thr Arg Asp Asp Tyr Gly
    130                 135                 140
```

-continued

```
Val Trp Glu Ile Phe Leu Pro Asn Asn Ala Asp Gly Ser Pro Ala Ile
145                 150                 155                 160

Pro His Gly Ser Arg Val Lys Ile Arg Met Asp Thr Pro Ser Gly Val
                165                 170                 175

Lys Asp Ser Ile Ser Ala Trp Ile Lys Phe Ser Val Gln Ala Pro Gly
                180                 185                 190

Glu Ile Pro Phe Asn Gly Ile Tyr Tyr Asp Pro Glu Glu Glu Lys
                195                 200                 205

Tyr Val Phe Gln His Pro Gln Pro Lys Arg Pro Glu Ser Leu Arg Ile
        210                 215                 220

Tyr Glu Ser His Ile Gly Met Ser Ser Pro Glu Pro Lys Ile Asn Ser
225                 230                 235                 240

Tyr Ala Asn Phe Arg Asp Glu Val Leu Pro Arg Ile Lys Arg Leu Gly
                245                 250                 255

Tyr Asn Ala Val Gln Ile Met Ala Ile Gln Glu His Ser Tyr Tyr Ala
                260                 265                 270

Ser Phe Gly Tyr His Val Thr Asn Phe Phe Ala Pro Ser Ser Arg Phe
        275                 280                 285

Gly Thr Pro Glu Asp Leu Lys Ser Leu Ile Asp Arg Ala His Glu Leu
        290                 295                 300

Gly Leu Leu Val Leu Met Asp Ile Val His Ser His Ser Ser Asn Asn
305                 310                 315                 320

Thr Leu Asp Gly Leu Asn Gly Phe Asp Gly Thr Asp Thr His Tyr Phe
                325                 330                 335

His Gly Gly Pro Arg Gly His His Trp Met Trp Asp Ser Arg Leu Phe
                340                 345                 350

Asn Tyr Gly Ser Trp Glu Val Leu Arg Phe Leu Leu Ser Asn Ala Arg
        355                 360                 365

Trp Trp Leu Glu Glu Tyr Lys Phe Asp Gly Phe Arg Phe Asp Gly Val
        370                 375                 380

Thr Ser Met Met Tyr Thr His His Gly Leu Gln Met Thr Phe Thr Gly
385                 390                 395                 400

Asn Tyr Gly Glu Tyr Phe Gly Phe Ala Thr Asp Val Asp Ala Val Val
                405                 410                 415

Tyr Leu Met Leu Val Asn Asp Leu Ile His Gly Leu Tyr Pro Asp Ala
                420                 425                 430

Val Ser Ile Gly Glu Asp Val Ser Gly Met Pro Thr Phe Cys Ile Pro
        435                 440                 445

Val Pro Asp Gly Gly Val Gly Phe Asp Tyr Arg Leu His Met Ala Val
        450                 455                 460

Ala Asp Lys Trp Ile Glu Leu Leu Lys Gln Ser Asp Glu Ser Trp Lys
465                 470                 475                 480

Met Gly Asp Ile Val His Thr Leu Thr Asn Arg Arg Trp Leu Glu Lys
                485                 490                 495

Cys Val Thr Tyr Ala Glu Ser His Asp Gln Ala Leu Val Gly Asp Lys
            500                 505                 510

Thr Ile Ala Phe Trp Leu Met Asp Lys Asp Met Tyr Asp Phe Met Ala
        515                 520                 525

Leu Asp Arg Pro Ser Thr Pro Arg Ile Asp Arg Gly Ile Ala Leu His
        530                 535                 540

Lys Met Ile Arg Leu Val Thr Met Gly Leu Gly Gly Glu Gly Tyr Leu
545                 550                 555                 560
```

-continued

```
Asn Phe Met Gly Asn Glu Phe Gly His Pro Glu Trp Ile Asp Phe Pro
                565                 570                 575

Arg Gly Pro Gln Thr Leu Pro Thr Gly Lys Val Leu Pro Gly Asn Asn
            580                 585                 590

Asn Ser Tyr Asp Lys Cys Arg Arg Phe Asp Leu Gly Asp Ala Asp
        595                 600                 605

Phe Leu Arg Tyr Arg Gly Met Gln Glu Phe Asp Gln Ala Met Gln His
    610                 615                 620

Leu Glu Glu Lys Tyr Gly Phe Met Thr Ser Glu His Gln Tyr Val Ser
625                 630                 635                 640

Arg Lys His Glu Glu Asp Lys Val Ile Ile Phe Glu Arg Gly Asp Leu
                645                 650                 655

Val Phe Val Phe Asn Phe His Trp Ser Asn Ser Lys Lys Asp Tyr Arg
                660                 665                 670

Val Gly Cys Ser Lys Pro Gly Lys Tyr Lys Val Ala Leu Asp Ser Asp
            675                 680                 685

Asp Ala Leu Phe Gly Gly Phe Ser Arg Leu Asp His Asp Val Asp Tyr
        690                 695                 700

Phe Thr Thr Glu His Pro His Asp Asn Arg Pro Arg Ser Phe Ser Val
705                 710                 715                 720

Tyr Thr Pro Ser Arg Thr Ala Val Val Tyr Ala Leu Thr Glu
                725                 730

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 3
acgcgtagat ctggcgccat ggcggaagta aa                                    32

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 4
cccgggtcta gatttttttt tttttttttt                                       30

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 5
atctggatcc atggcggaag taaaca                                           26

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:Description
``` of Artificial SequencE: synthetic primer

<400> SEQUENCE: 6
gagtatccat ccgtatctt                                                19

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 7
atgcccttac agagcaccac caccaccacc actaagaacc agcagct                 47

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 8
atgtgagagc tcggatggtt cagtgcag                                      28

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 9
tatgataaat gccgccgtag a                                             21

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 10
gtgtggaatt gtgagcggat aac                                           23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Description
      of Artificial SequencE: synthetic primer

<400> SEQUENCE: 11
tgagccacgc agaagtacag aatg                                          24

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:Description
      of Artificial SequencE: synthetic primer

```
<400> SEQUENCE: 12
atcatcgcaa gaccggcaac ag                                                              22
```

TRANSGENIC CORN PLANTS HAVING SEEDS WITH MODIFIED CORNSTARCH CHARACTERISTICS AND METHOD OF MAKING THE TRANSGENIC CORN PLANTS

CROSS-REFERENCE TO RELATED APPLICATION

This application claims the benefit of U.S. provisional application Ser. No. 60/295,649, filed on Jun. 4, 2001.

STATEMENT REGARDING FEDERALLY SPONSORED RESEARCH OR DEVELOPMENT

Not applicable.

BACKGROUND OF THE INVENTION

Starch is a polymer of glucose linked by $\alpha(1-4)$ linkages to give linear chains, H which are joined by $\alpha(1-6)$ linkages resulting in branches in the polymer. Normal starch consists of about 75% amylopectin, a highly-branched molecule, and 25% of amylose, a primarily linear molecule. These polymers are organized into an insoluble granule within cereal seeds. Starch granules are highly organized, containing of a series of concentric spheres consisting of alternating crystalline and amorphous regions (Cameron and Donald, 1992).

Starch is synthesized by a series of enzymatic reactions (for review, see Martin and Smith, 1995; Myers et al., 2000). Glucose-1-phosphate is first activated to ADP-glucose by the enzyme ADP-glucose pyrophosphorylase (ADPGPP). This enzyme is heavily regulated and is thought to control the flux of carbon into starch biosynthesis, and therefore the amount of starch made. The structure of starch is determined by the subsequent enzymes in the pathway. Starch synthases (SS) catalyze the polymerization of ADP-glucose to produce a linear glucan polymer. Branches are introduced into this polymer by starch branching enzymes (SBE). Starch debranching enzymes (SDBE) contribute to starch structure by removing excess branches, which may help to establish the pattern of crystalline and amorphous regions within the granule.

Starch structures differ in different species. For example, barley and wheat amylopectins have larger portions of short branch chains (6 to 14 glucose units), have proportionally fewer branch chains of 11 to 22 glucose units and >40 glucose units, and larger proportions of branch linkages located within the crystalline region than maize amylopectin (Jane et al., 1999; Song and Jane, 2000). It is the starch structure that determines the functionality of starch.

The higher starch yield of corn as a C-4 crop makes cornstarch the most economic commodity in the world. Starch is easily isolated from corn seeds during milling process as compared to barley or wheat whose awns or gluten makes starch separation more difficult. In addition, the higher phospholipid content of barley and wheat starches restricts starch swelling and paste viscosity. However, barley or wheat starches have lower gelatinization temperatures than cornstarch, and thus require less energy for processing and cooking (Jane et al., 1999). Compared to cornstarch, barley or wheat starch has a lower retrogradation rate during storage, which translates into better paste stability and prolonged shelf life (Shi and Seib, 1992,1995; Yuan et al., 1993; Jane et al., 1999). Barley and wheat starches are also easier to digest by enzyme and animals than cornstarch, which can result in faster glucose production from starch and increased energy availability to livestock. This is particularly beneficial to young and small animals such as baby chicks that have shorter digestive tracts.

Chemical modifications of starch (e.g. chemical derivatives) are commonly used in the wet-milling industry to reduce the gelatinization temperature and retrogradation rate. Chemical modification processes are energy demanding, requiring large quantities of chemical reagents and salts during the reaction and washing and drying after the reaction. Recovery of byproducts, unreacted reagents, and salts (e.g. sodium sulfate) from wastewater is costly and has the potential to cause environmental pollution.

Genetic modification of starch structure provides an attractive alternative to improve functionality. It was estimated that genetic modification of cornstarch structure and functionality could add value $1.25 billion per year, with an average added value of $5.80 per bushel (Johnson et al., 1999a). An increase of cornstarch digestibility by 10% for livestock feed would add another $1.44 billion per year, with an average added value of $0.21 per bushel (Johnson et al., 1999b). In addition, genetically modified corn may be used to make possible new starch products (such as biodegradable plastics) and create new markets.

Genes or cDNAs of most starch biosynthetic enzymes have been cloned in corn, potato, barley, and wheat. They can be used to over- or under-express these enzymes by using sense or antisense transgenes. Expression of an *E. coli* ADPGPP in potato tubers increased starch content by 35% (Stark et al., 1992). Transformation of the amylose deficient amf mutant of potato with the granule-bound starch synthase (GBSS) gene led to amylose synthesis (Flipse et al., 1994), whereas various levels of reduction in GBSS protein and amylose were observed in transgenic rice endosperm with the antisense GBSS gene connected to the rice GBSS promoter or maize Adhl promoter (Terada et al., 2000). Antisense inhibition of two soluble SS of potato individually or simultaneously led to distorted starch granules and an enrichment in short chains and a reduction in longer chains of amylopectin (Edwards et al., 1999; Lloyd et al., 1999). Expression of an *E. coli* branching enzyme in tubers of amylose-free potato showed an increased branching degree and more short chains (16 glucose-residues or less) of the amylopectin (Kortstee et al., 1996). The antisense inhibition of the main SBE in potato tubers (SBE B) resulted in novel starch characteristics but not in an increased amylose level (Safford et al., 1998). However, transgenic potato plants expressing an antisense SBE A (the minor form of SBE) RNA increased the average chain length of amylopectin, resulting an moderate increase in apparent amylose content up to 38% (Jobling et al., 1999). Antisense inhibition of both SBE A and B simultaneously led to the production of potato starch with high-amylose and no amylopectin (Schwall et al., 2000).

There is a need in the art for a method of producing cornstarch combining the advantages and avoiding the disadvantages of corn and barley starches using genetic engineering.

BRIEF SUMMARY OF THE INVENTION

The present invention is summarized in that cornstarch characteristics can be changed by expressing a non-corn plant SBE in a corn plant. In one aspect, the present invention is a transgenic corn plant that contains a polynucleotide transgene. The transgene encodes a protein having a non-corn plant SBE activity wherein the expression of the protein in a corn plant can change a cornstarch characteristic as compared to a plant of the same genetic background without the polynucleotide transgene. A transgenic plant cell or tissue including a seed that contains the polynucleotide transgene is also within the scope of the present invention.

In another aspect, the present invention is a method of generating a transgenic corn plant wherein seeds from the transgenic corn plant contain cornstarch with a changed characteristic. The method involves contacting a corn plant cell with a nucleic acid that contains a polynucleotide encoding a protein that has a non-corn SBE activity, identifying a plant cell carrying the polynucleotide, and regenerating a transgenic plant from the plant cell identified. A plant obtained by the method of the present invention and cells and tissues including seeds of the plant are also within the scope of the present invention.

It is an advantage of the present invention that the cornstarch characteristics are changed using genetic engineering so that potential environmental pollution problems associated with chemical modifications of starches in changing starch characteristics are avoided.

It is another advantage of the present invention that the method of modifying cornstarch characteristics is easy and cost effective in comparison to prior art chemical modification methods.

Compared with the starches of corn mutants affecting starch composition in endosperm, starches from transgenic plant can provide a wide range and combinations of starch structure and functionality to meet needs of the food and industrial applications.

Other objects, advantages and features of the present invention will become apparent from the following specifications and claims.

DETAILED DESCRIPTION OF THE INVENTION

Figure 1:
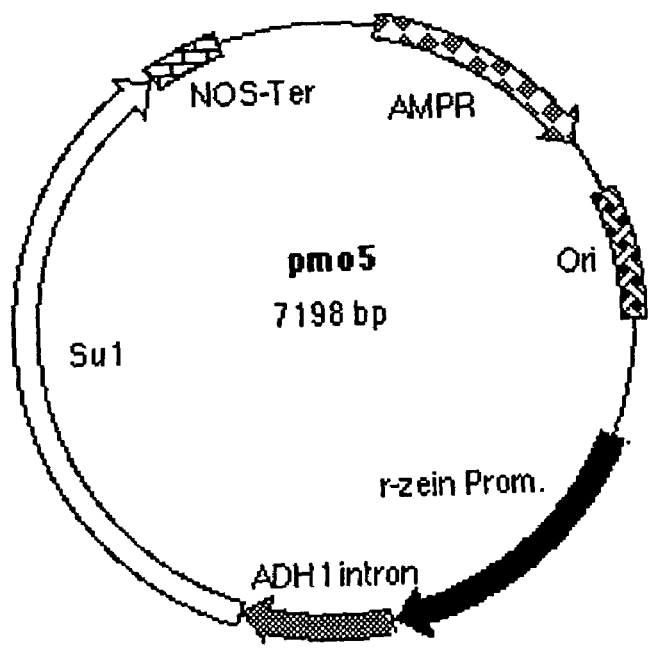
FIG. 1 is a map of the pMO5 plasmid.

The present invention relates to using genetic engineering to change cornstarch characteristics, which involves generating transgenic corn plants that express a polynucleotide encoding a protein that has a non-corn plant SBE activity. A non-corn plant SBE activity is defined herein as the activity of an SBE from a plant other than a corn plant. The expression of the polynucleotide in a corn plant may change cornstarch characteristics in one of two ways. One, the non-corn plant SBE activity can cause cornstarch to have characteristics closer to starch from a plant in which the non-corn plant SBE is natively expressed. Two, when the expression level of the polynucleotide in the transgenic plant is above a certain threshold level leading to silencing of all branching enzyme activities, cornstarch produced from the transgenic plant will have a higher gelatinization temperature and retrogradation rate; the cornstarch will also have a higher amylose content and thus share functional characteristics of high-amylose starch.

The present invention is illustrated in the example below with barley SBE IIa. Barley starch has a lower starch gelatinization temperature and retrogradation rate in comparison to cornstarch. Expressing barley SBE IIa in a corn plant led to lower starch gelatinization temperature and retrogradation rate in some corn plants and higher retrogradation rate in other corn plants.

To make a transgenic corn plant that expresses a polynucleotide encoding a non-corn plant SBE activity, as is known to those of skill in the art, one needs to make a genetic construction capable of expressing the polynucleotide in a corn plant. One also needs a method to insert the genetic construction into the plant.

The tools and techniques for making genetic constructions that will express proteins in plants are now widely known. Any genetic construction intended to cause the synthesis in the cells of the plant of a polypeptide or protein must include a sequence of DNA known as a protein coding sequence (can be a genomic DNA or a cDNA), which specifies the sequence of the polypeptide or protein to be produced in the resultant plant. For a protein coding sequence to be expressed in a plant to produce a polypeptide or protein, it must be placed under the control of a plant expressible promoter and be followed by a plant transcriptional terminator sequence, also known as a polyadenlyation sequence. The plant expressible promoter is a promoter which will work in plants, usually either of plant origin or from a plant pathogen like a virus (e.g. Cauliflower mosaic virus) or a bacteria (e.g. *Agrobacterium* promoters like the nopaline synthase promoter).

Plant promoters from pathogens tend to be constitutive promoters, meaning that they actually express the protein coding sequence in all of the tissues of the plant at all times. Examples of constitutive promoters useful in plant genetic constructions include, without limitation, the 35S RNA and 19S RNA promoters of the Cauliflower mosaic virus (Brisson et al., Nature, 310, 511, 1984), and the opine synthase promoters carried on the tumor-inducing plasmids of *Agrobacterium tumefaciens* such as the nopaline synthase promoter (Ebert et al., PNAS, 84, 5745, 1987) and the mannopine synthase promoter (Velten et al., EMBO J. 3, 2723 1984).

Other plant promoters are known to be tissue specific or developmentally specific, while others are intended to be inducible (e.g. heat shock or metal ion induced promoters). An example of tissue specific promoters is the maize γ-zein promoter used in the example below for expressing genes in endosperm. Endosperm specific promoters are preferred promoters for the present invention. Examples of inducible promoters suitable for use in the present invention include, but are not limited to, heat shock promoters such as soybean hsp17.5E or hsp17.3 (Gurley et al., Mol. Cell Biol. 6, 559, 1986), light-regulated promoters such as the promoter for the small subunit or ribulose bisphosphate carboxylase (ss-RUBISCO) (Coruzzi et al., EMBO J. 3, 1671, 1984; Broglie et al., Science 224, 838, 1984), chemical-regulated promoters such as Maize In2-1 and 2-2 which are regulated by benzenesulfonamides, e.g., herbicide safeners (Hershey et al., Plant Mol. Biol., 17, 679, 1991), and alcA and alcR promoter/transcription factor system that is induced by the application of ethanol (Caddick et al., Nat. Biotech., 16, 177, 1998).

Any of the promoters described above may be used in the practice of this invention depending on the intended effect on the transgenic corn plant to be produced. For example, adjusting the expression level of a polynucleotide encoding a non-corn plant SBE activity by varying promoter strength may determine the likelihood of the transgenic plant to have the non-corn plant SBE activity or to have all branching enzyme activities silenced.

Optionally, a selectable marker may be associated with a genetic construct used to generate a transgenic plant. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase, and amino-glycoside 3'-O-phosphotransferase II (which confers kanamycin, neomycin and G418 resistance). Other suitable markers will be known to those of skill in the art.

Several methods have been demonstrated to insert genes into plants to make them transgenic. The most widely used methods, broadly defined, are *Agrobacterium*-mediated transformation and accelerated particle mediated transformation (as illustrated in the example below). The various techniques of *Agrobacterium*-mediated plant transformation make use of the natural ability of the plant pathogens of the *Agrobacterium* genus to transfer DNA from a plasmid in the bacteria into the genome of a plant cell. Particle-mediated plant transformation techniques utilize DNA-coated small carrier particles accelerated from a device, often referred to as a gene gun, into the cells of a plant. The full implementation of either approach requires techniques to recover a fully mature, morphologically normal plant from the transformed cells. The techniques often therefore involve either selection or screening protocols to identify which plant cell was transformed and regeneration protocols to recover a whole plant from a single transformed plant cell. As mentioned above, these techniques have been worked out for many plant species and many, and perhaps all, of the economically important plant species including corn plants.

Viruses such as the Cauliflower mosaic virus (CaMV) may also be used as a vector for introducing a transgene into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid again may be cloned and further modified by introduction of the desired polynucleotide sequence. The modified viral portion of the recombinant plasmid is then excised from the parent bacterial plasmid, and used to inoculate the plant cells or plants.

Other techniques, such as electroporation have also been used to make transgenic plants. But fundamentally for the invention disclosed here, the particular technique of plant transformation does not matter. Once the plant has been genetically engineered, and a transgenic plant has been created, the method of transformation of the original plant becomes irrelevant. A transgene inserted into the genome of one plant is then fully inheritable by progeny plants of the original genetically engineered plant by normal rules of classical plant breeding. For example, in vegetatively propagated crops, the mature transgenic plants are propagated by the taking of cuttings or by tissue culture techniques to produce multiple identical plants. Selection of desirable transformed plants is made and new varieties are obtained and propagated vegetatively for commercial use. In seed-propagated crops, the mature transgenic plants can be self crossed to produce a homozygous inbred plant. The inbred plant produces seed containing the newly introduced transgene. These seeds can be grown to produce plants that would produce the selected phenotype.

It should be understood that techniques of plant genetic engineering have been developed to the point where it is now practical to place any genetic construct into almost any useful plant species including corn plants. The process does, however, still involve some random processes, most notably that insertions of foreign DNA into the genome of plants still occurs at random sites in the plant genome. As a result, in any group of plants emerging from a plant transformation process, the results achieved for the different gene insertion events will vary, sometimes dramatically, depending on where the transgene is inserted. However, this variation does not mean stable results cannot be achieved, since the results tend to be consistent generation-to-generation for each specific genetic insertion. One can also take advantage of this variation to generate lines with cornstarch characteristics changed to different degrees. As shown in the example below, when barley sbe IIa was used to generate transgenic corn plants, cornstarch from some transgenic plants had lower gelatinization temperature and retrogradation rate while cornstarch from other transgenic plants had higher retrogradation rate. For those transgenic plants with cornstarch of lower gelatinization temperature and retrogradation rate, the degree to which the gelatinization temperature and retrogradation rate were lowered were different.

The transgenic corn plants created by the methods described above, the seeds of which contain starch with changed characteristics, are within the scope of the present invention. Progeny and parts obtained from the plant such as seeds, are included in the invention, provided that the progeny and the parts comprise cells that contain the transgene.

SBEs of different species provide starches obtained from these species with different characteristics. The present invention offers the opportunity to combine the advantages and avoid disadvantages of starches from two different species. The novel starches produced may add value to the corn crop for the existing uses, or create new products and new markets for starch such as biodegradable plastics. When starch from a particular non-corn plant species has a desirable characteristic attributable to its SBE that is absent from cornstarches, a polynucleotide encoding a protein that has the SBE activity can be used to generate transgenic corn plants from which one that produces starch with the desired characteristic can be selected. The polynucleotide can be the SBE gene itself. One of ordinary skill in the art will appreciate that certain variations on the gene such as point mutations, insertions and deletions will not abolish the specific SBE activity of the gene. Accordingly, these gene variants can also be used to generate a transgenic corn plants in the present invention. Given the potential silencing effect of an overexpression of the polynucleotide on all branching enzyme activities, the same transgenic plants above can also be used to select for plants that produce starches with a higher gelatinization temperature and retrogradation rate and for plants that produce starches with a high amylose content.

In one embodiment, a barley sbe IIa or a variant thereof that retains the specific SBE IIa enzymatic activity is used to generate transgenic corn plants for producing cornstarch with lower starch gelatinization temperature and retrogradation rate or cornstarch with higher amylose content and retrogradation rate. Lower starch gelatinization temperature and small enthalpy changes reduce energy consumption for starch cooking. Lower retrogradation rate of starch results in a better paste stability, and longer shelf life. It may also help retain water biding capacity and thickening power and results in superior paste properties as a sizing agent used in paper, textile, and other industries. High amylose starch has many applications in the industry for its unique functional properties, and starches with high retrogradation rate may be used to produce resistant starch for low caloric diet.

In other embodiments, other genes or a variant thereof are used for changing cornstarch characteristics. Examples of these genes include but are not limited to barley sbeIIb (Genebank Accession Number AF064561), wheat sbe1A (Genebank Accession Number AF286318), wheat sbe1D (Genebank Accession Number AF286317), wheat sbeIIa-1 (Genebank Accession Number Y11282), wheat sbeIIa-2 (Genebank Accession Number U66376), wheat sbe2 (Genebank Accession Number AF286319), wheat sbe as disclosed in WO0132886 (Genbank Accession Number AX134202), rice sbeI (Genebank Accession Number D11082), rice sbe3 (Genebank Accession Number D16201), pea sbeI (Genebank Accession Number X80009), pea sbeII (Genebank Accession Number X80010), a potato sbe, *Arabidopsis* sbe2-1 (Genebank Accession Number U11817), and *Arabidopsis* sbe2-2 (Genebank Accession Number U22428). Branching enzymes found in bacteria including *Bacillus* bacteria can also be used (e.g., Genebank Accession Numbers Z14057, Z25795, and AF008220). Sun et al. 1995 compares some of the genes listed above and is herein incorporated by reference in its entirety.

The invention will be more fully understood upon consideration of the following non-limiting example.

EXAMPLE

Materials and Methods

Construction of pMO5 vector: A plasmid 27.3-D was a kind gift from Dr. Brian Larkins' lab (University of Arizona), which contains the promoter of the maize gamma zein gene (Reina et al., 1990, which incorporated herein by reference in its entirety) in a pUC19 backbone. A SacI-EcoRI fragment containing the Nos terminator of *Agrobacterium tumefaciens* was sub-cloned from pBI101.3 (Clontech, Palo alto, Calif.) into 27.3-D to form pMO1. Subsequently, the first intron of maize AdhI gene was introduced into pMO1 to derive pMO2. The full-length cDNA of maize Su1 gene (James et al., 1995) was inserted into the NcoI-NotI sites of pMO2 to create pMO5 (FIG. 1).

Figure 2:
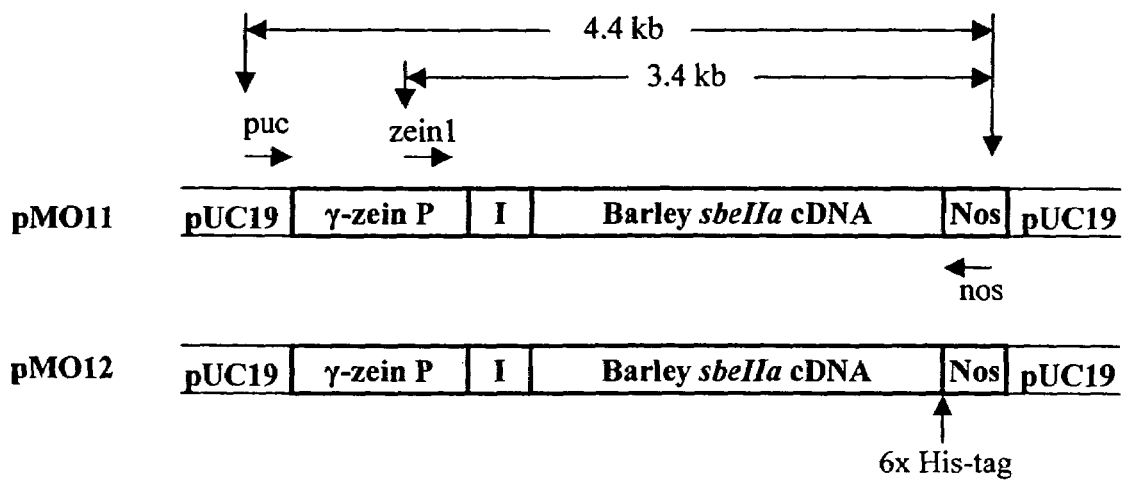
FIG. 2 shows barley sbeIIa gene constructs and primers used to amplify the transgene. The constructs have a maize γ-zein promoter (γ-zein P), first intron of maize adhl gene (I), full-length barley sbeIIa cDNA, and terminator region from *A. tumefaciens* nopaline synthase gene (Nos), and is built on a pUC19 backbone. Primers puc, zein1, and nos were used to amplify a 3.4 or 4.4 kb transgene product. Vector pMO12 has a 6×His-tag just before the stop codon of the sbeIIa gene.

Construction of Barley SBE IIa Expression Vectors: For expression of barley SBE in corn, the barley sbeIIa cDNA (GenBank Accession Number AF064560, provided as SEQ ID NO:1 herein) (Sun et al., 1998) was amplified by PCR with Taq DNA polymerase using the upper primer (5'-ACGCGTAGATCTGGCGCCATGGCGGAAGTAAA-3') (SEQ ID NO:3) and the lower primer (5'-CCCGGGTCTA-GATTTTTTTTTTTTTTTTTT-3') (SEQ ID NO:4). The PCR product was cloned into pTAg plasmid (R & D Systems, Minneapolis, Minn.). Primers BM1 (5'-ATCTG-GATCCATGGCGGAAGTAAACA-3') (SEQ ID NO:5) and BM2 (5' -GAGTATCCATCCGTATCTT-3') (SEQ ID NO:6) were used to amplify a 527-bp PCR fragment from the sbeIIa clone with Expand™ High Fidelity PCR system (Roche Molecular Biochemicals, Indianapolis, Ind.), and the fragment was digested by BamHI and was cloned into the BamHI site of a plasmid pMO5. The resulting plasmid was then cut with BamHI and SacI to accept a 1.8 kb BamHI/SacI fragment of the sbeIIa clone. This plasmid was further digested with SacI to accept a SacI/SacI fragment amplified from sbeIIa clone using primers BM4 (5'-ATGCCCTTA-CAGAGCACCACCACCACCACCACTAA-GAACCAGCAGCT-3') (SEQ ID NO:7) and BM5 (5'-AT-GTGAGAGCTCGGATGGTTCAGTGCAG-3') (SEQ ID NO:8), resulting vector pMO11 (FIG. 2).

To add a 6×-histidine tag to the C-terminus of the barley sbeIIa clone, primer BM4 and BM5 were used to amplify a 295 bp PCR product from the barley sbeIIa clone. The PCR fragment was further used as "megaprimer" to amplify a 701 bp PCR product from the sbeIIa clone with primer BM3 (5'-TATGATAAATGCCGCCGTAGA-3') (SEQ ID NO:9). The resulting PCR product was digested with EcoRV and SacI restriction enzymes, and was cloned into pMO11 cut with the same enzymes. The plasmid was then digested with SacI to accept a SacI/SacI fragment from the PCR product amplified by BM4 and BM5. The plasmid generated has a 6×-histidine tag just before the stop codon of barley sbeIIa cDNA and was named pMO12 (FIG. 2). Plasmids pMO11 and pMO12 were both sequenced to ensure that no mutation was introduced and the restriction fragments ligated are in correct orientation.

Maize Transformation and Analyses: The maize transformation was conducted using particle bombardment method at the Plant Transformation Facility of Iowa State University according to standard procedures (Fromm, 1994). Immature embryos of Hi II hybrid and Oh43 inbred were used for the transformation. Gold particles coated with 1 μg plasmid DNA were used to bombard embryogenic callus tissue with an instrument from Biolistics (Ithaca, N.Y.). A *Streptomyces* bar gene on a separate plasmid was co-bombarded as a selectable marker. The bar gene is expressed constitutively from the maize ubiquitin promoter, with transcription termination occurring from the *A. tumefaciens* 3' nos region. Successfully transformed calli were identified by growth on media containing the selective reagent Bialaphos at 3 mg/L. Approximately 20 clones (independent transgenic events) for each construct were regenerated into Plants. Primary regenerated plants (R0) were outcrossed to both Oh43 inbred and Oh43 with homozygous amylose extender (ae) mutant alleles.

DNA was extracted from callus tissue and leaves of regenerated plants by using the method of Dellaporta (1994) (incorporated by reference in its entirety) with the following modifications. The extraction buffer contained 100 mM Tris, pH 8.0, 50 mM EDTA, pH 8.0, 500 mM NaCl, 10 mM beta-mercaptoethanol, and 1% SDS. Callus tissue was ground in the extraction buffer in the presence of about 10 mg carborundum (Fisher Scientific, Pittsburgh, Pa.) instead of liquid nitrogen. DNA was dissolved in 10 mM Tris-HCl, pH 8.0. An RNase treatment was added to the DNA isolation protocol as follows. The DNA isolated was treated with RNase A (Sigma, St. Louis, Mo.) at 100 μg/ml for 15 min at 37° C. Then 1 μl of 5 M NaCl per 20 μl DNA and three volumes of 100% ethanol were added. After 10 min on ice, samples were spun at 13,000 g for 10 min. The pellet was washed with 70% ethanol, air or vacuum dried, and resuspended in 10 mM Tris-HCl (pH 8.0).

PCR analysis was used to screen the callus clones and confirm the presence of intact copies of transgenes in the regenerated plants. Two sets of primers (FIG. 2) were used to amplify the transgene products with Expand™ Long Template PCR System (Roche Molecular Biochemicals, Indianapolis, Ind.) that is composed of a mixture of Taq and Pwo DNA polymerases. Primer, puc is a 23-mer (5'-GT-GTGGAATTGTGAGCGGATAAC-3') (SEQ ID NO:10), zein1 is a 24-mer (5'-TGAGCCACGCAGAAGTACA-GAATG-3') (SEQ ID NO:11), and nos is a 22-mer (5'-ATCATCGCAAGACCGGCAACAG-3') (SEQ ID NO:12).

Manufacturer's buffer 1 and 500 ng of template DNA were included in the reaction mixtures. The PCR reactions were run in a Mastercycler® personal thermocycler (Eppendorf Scientific, New York, N.Y.) with an initial denaturation for 2 min at 94° C.; followed by 30 cycles of 94° C. for 20 s, 65° C. for 30 s, and 68° C. for 2 min 20 s (zein1 and nos primer pair) or 3 min (puc and nos primer pair). From the 11th cycle, each cycle had 20 s more elongation time at 68° C. than the previous cycle. The reaction was concluded with a prolonged elongation time of 7 min at 68° C. A 3.4 kb or 4.4 kb PCR fragment of barley SBEIIa transgene was robustly amplified. The fragments cover the length of the entire transgene (FIG. 2).

Assay of Branching Enzyme Activity: Kernels were isolated from developing ears 20 days after pollination and were immediately frozen in liquid nitrogen before being stored in freezer. Individual seeds were ground in a tube containing 2.5 ml/g extraction buffer (50 mM Tris-HCl, pH 7.0; 10% glycerol; 10 mM EDTA; 5 mM DTT, and 1% proteinase inhibitor cocktail (#P-9599) from Sigma) using a hand drill connected with a microfuge pestle (Kontes Sci., Vineland, N.J.; item number 749520) and vortexed. The homogenate was spun at 10,000 g for 10 min at 4° C. and the supernatant was saved. Protein concentration was determined according to the method of Bradford (1976) using a Bio-Rad Protein Assay Kit with BSA as the standard.

Branching enzyme activity was measured by the phosphorylation-stimulation assay (Sun et al., 1997, incorporated by reference in its entirety) using 20 μg seed protein. The amount of branching enzyme was in the linear range with the rate of phosphate release. A control with 20 μg of boiled yeast protein was also incubated. The small amount of Pi produced in the control was subtracted from those produced in samples with active branching enzyme present.

Isolation and Analyses of Starch: Mature seeds were weighed and steeped in 0.45% sodium metabisulfite for 48 hrs at room temperature. Single seed was homogenized in 10 ml water with a Ultra-Turrax T25 homogenizer (Janke & Kunkel, Staufen, Germany) for 1 min, after seed coat and embryo were removed. The homogenate was centrifuged at 50,000 g for 30 min to separate the soluble material in the supernatant and starch in the pellet. The starch-containing pellet was resuspended in about 200 ml water, passed through a 53 μm nylon mesh filter (Spectrum, Laguna Hills, Calif.) into a beaker. The starch was sedimented at 4° C. for 2 hrs and the supernatant was decanted. The sediments were then stirred up with 200 ml fresh water. The sedimentation and decanting were performed four times. After last decanting, the starch was dried at room temperature and weighed.

Gelatinization and retrogradation properties of starches were analyzed by using a differential scanning calorimeter (DSC-1, Perkin-Elmer, Norwalk, Conn.) equipped with an intracooling II system as described by Jane et al. (1999), which is incorporated by reference in its entirety. The data were averages of three replicates of each starch sample. Analysis of variance was used for data analysis (Steel and Torrie, 1960). Mean differences were compared by using least significant differences (LSD) at both the 5% and 1% levels of probability.

Results

Callus clones were screened for the presence of transgenes by PCR using primers that cover the entire length of the transgene (FIG. 2). Most clones had the intact copy of the transgene, but some clones had no transgene or only rearranged/truncated copies. Only those clones with intact transgene copies were selected for regeneration into plants. We have obtained a total of 31 clones (independent transgenic events). The presence of intact transgenes in regenerted plants was confirmed by PCR analyses of leaf DNA.

Most regenerated plants look normal. These $R_0$ plants, mostly as females, were outcrossed to both OH43 inbred and aeae mutant in OH43 inbred background to get $R_1$ seeds. Of the 31 clones we obtained, 11 showed various degree of translucent and shrunken kernel phenotype in about half of the seeds on an ear, especially when crossed to an aeae male plant.

Starches were isolated from single $R_1$ seeds and their thermal properties were measured by differential scanning calorimetry (DSC). Results from some selected clones are presented in Table 1. Starches of clone P90-4×OH43 inbred displayed lower onset gelatinization temperatures than starches from the untransformed control. Their thermal transition peak of starch gelatinization initiated at a substantially lower temperature of about 55° C., compared with above 60° C. for the untransformed control. Starches isolated from the slightly shrunken kernels of clone P90-4× OH43 displayed high completion temperatures and large ranges of gelatinization temperature. The wide peaks of the thermal profiles for these starches resemble that of aeae mutant or high amylose starches (Wang et al., 1992; Kasemsuwan et al., 1995; Jane et al., 1999). These kernel phenotypes and DSC profiles were also observed in crosses of P90-4 to aeae mutant and were not found in untransformed control crosses. The results indicated that these features were not likely caused by the ae mutant allele but were resulted from the transgenes. Starches from some seeds of clones P90-4, P90-8 and P90-15 had substantially smaller enthalpy change than the untransformed controls, and the value for a seed from P90-2×OH43 cross was only 30% of the controls.

All the clones we analyzed had some seeds with lower starch retrogradation rate than the untransformed controls (Table 1). On the other hand, starches from some seeds showed much higher retrogradation rate than the controls, sometimes reaching 100%. Their retrogradation profiles are similar to that of aeae mutant or other high amylose maize starches as reported by others (Kasemsuwan et al., 1995; Jane et al., 1999).

Branching enzyme activities showed a wide range of variations, ranging from almost no activity to double of the untransformed controls (Table 1). Without intending to be limited by theory, we hypothesize that these variability may explain some of the variations in thermal properties displayed by some seeds. Expression of the barley sbe IIa gene may lower the gelatinization temperature and retrogradation rate, making the cornstarch function more like barley starch. When the expression of the barley BE gene exceeds certain threshold level, however, it may cause silencing of all BE genes. Gene silencing effect may reduce the BE activities in the kernel and lead to the production of high-amylose starch like aeae mutant. It is well established that overexpression of transgenes may lead to gene silencing. Linked and unlinked copies of transgenes and related endogenous genes in plants can be epigenetically silenced by homology-based mechanisms that operate at either the transcriptional or post-transcriptional level (Matzke et al., 1996; Matzke and Matzke, 1998). All SBEII gene family members from wheat, barley, maize, rice, pea, and *Arabidopsis* share a high degree of amino acid identity (90%–95%) in the major portion of their coding sequences (Sun et al., 1998). Silencing of the granule-bound starch synthase I (GBSSI) in potato has been achieved by introduction of either antisense or sense copies of GBSSI cDNA or genomic DNA (Wolters and Visser, 2000). Compared with crosses with OH43 inbred, kernels from crosses with aeae mutant have reduced Ae (endogenous SBEIIb) allele in their endosperm and thus reduced competition with the barley SBEIIa transgene. That may allow the barley BE gene to have more pronounced effect.

Indeed, most translucent and sunken kernel phenotype was observed in crosses with aeae mutant.

A wide range of genetic variation in starch BE activities and thermal properties has been observed in the corn kernels transformed with barley SBEIIa gene. Lower starch gelatinization temperature and small enthalpy changes reduce energy consumption for starch cooking. Lower retrogradation rate of starch results in a better paste stability, and longer shelf life. It may also help retain water biding capacity and thickening power and results in superior paste properties as a sizing agent used in paper, textile, and other industries. High amylose starch has many applications in the industry for its unique functional properties, and starches with high retrogradation rate may be used to produce resistant starch for low caloric diet.

The present invention is not intended to be limited to the foregoing example, but encompasses all such modifications and variations as come within the scope of the appended claims.

REFERENCES

Bradford M M. (1976) A rapid and sensitive method for the quantitation of microgram quantities of protein utilizing the principle of protein-dye binding. Anal Biochem. 72:248–254.

Cameron R E, Donald A M. (1992) A small-angle X-ray scattering study of the annealing and gelatinization of starch. Polymer 33:2628–2635.

Dellaporta S. (1994) Plant DNA miniprep and microprep: Version 2.1–2.3. Method II, pp. 524–525. In M. Freeling and V. Walbot (Eds.), The Maize Handbook. Springer-Verlag Inc., New York, N.Y.

Edwards A, Fulton D C, Hylton C M, Jobling S A, Gidley M, Rossner U, Martin C, Smith A M. (1999) A combined reduction in activity of starch synthases II and III of potato has novel effects on the starch of tubers. Plant J 17(3):251–261.

TABLE 1

Thermal properties of starches measured by differential scanning calorimetry and branching enzyme (BE) activities of $R_1$ kernels from independent transgenic clones

| Genotype[a] | Kernel phenotype[b] | Kernel weight mg | Starch Gelatinzation[c] | | | | | Starch Retrogradation[d] | | | | | BE Specific activity[e] |
|---|---|---|---|---|---|---|---|---|---|---|---|---|---|
| | | | $T_o$ °C. | $T_p$ °C. | $T_c$ °C. | Range °C. | ΔH J/g | $T_o$ °C. | $T_p$ °C. | $T_c$ °C. | ΔH J/g | R % | % of control |
| Hill untran. control × OH43 | N | 212.3 | 68.0 | 71.7 | 75.7 | 7.7 | 12.0 | 37.9 | 49.4 | 61.9 | 6.8 | 56.4 | 95.9 |
| | N | 236.4 | 67.8 | 70.8 | 74.3 | 6.5 | 12.7 | 39.3 | 49.8 | 62.1 | 7.0 | 55.4 | 95.9 |
| | N | 150.1 | 68.0 | 71.9 | 76.0 | 8.0 | 12.4 | 38.7 | 49.5 | 62.3 | 7.3 | 59.2 | 84.2 |
| | N | 135.0 | 67.6 | 71.4 | 75.4 | 7.8 | 12.4 | 40.1 | 50.3 | 62.4 | 7.8 | 62.8 | 124.0 |
| P90-2 × OH43 | N | 328.4 | 66.9 | 71.7 | 75.1 | 8.2 | 11.9 | 42.0 | 52.7 | 62.4 | 5.6 | 47.5 | 9.4 |
| | N | 232.5 | 70.1 | 73.1 | 76.2 | 6.1 | 12.6 | 42.9 | 54.1 | 63.2 | 6.2 | 49.3 | 44.4 |
| | N | 271.0 | 69.0 | 74.2 | 82.2 | 13.2 | 3.8 | 47.5 | 57.0 | 63.6 | 1.4 | 36.4 | 4.7 |
| | N | 318.4 | 68.1 | 71.9 | 75.3 | 7.2 | 11.3 | 42.5 | 52.7 | 61.5 | 5.6 | 49.3 | 21.1 |
| P90-4 × OH43 | N | 337.6 | 64.0 (55.7) | 70.4 | 75.0 | 11.0 | 11.9 | 38.3 | 52.2 | 60.9 | 6.2 | 52.0 | 233.9 |
| | N | 219.6 | 66.3 (55.3) | 70.5 | 74.7 | 8.4 | 12.5 | 41.0 | 51.7 | 61.9 | 5.5 | 44.4 | 212.9 |
| | SS | 230.1 | 66.5 (55.1) | 72.4 | 88.9 | 22.4 | 14.3 | 41.7 | 56.4 | 111.0 | 47.8 | 100.0 | 84.2 |
| | SS | 283.6 | 66.1 (55.1) | 72.7 | 102.8 | 36.7 | 11.9 | 39.9 | 54.9 | 104.7 | 26.9 | 100.0 | 44.4 |
| P90-8 × OH43 | N | 169.8 | 67.4 | 71.5 | 77.2 | 9.8 | 12.9 | 42.1 | 52.7 | 61.8 | 6.8 | 52.3 | 117.0 |
| | N | 167.3 | 68.4 | 72.0 | 76.5 | 8.1 | 13.6 | 42.1 | 53.1 | 61.6 | 7.3 | 54.0 | 121.6 |
| | SS | 149.1 | 67.4 | 72.5 | 79.7 | 12.3 | 8.0 | 44.1 | 53.7 | 63.5 | 3.1 | 37.7 | 84.2 |
| | SS | 141.4 | 67.0 | 72.7 | 81.0 | 14.0 | 7.5 | 44.6 | 56.5 | 63.6 | 2.6 | 34.6 | 161.4 |
| Hill untran. Control × OH43aeae | N | 228.1 | 67.5 | 72.7 | 77.3 | 9.8 | 13.6 | 40.8 | 52.2 | 62.7 | 7.5 | 55.4 | 108.0 |
| | N | 253.6 | 68.0 | 72.4 | 76.9 | 8.9 | 12.8 | 41.7 | 52.3 | 62.4 | 7.7 | 60.0 | 98.4 |
| | N | 234.2 | 68.2 | 72.5 | 76.9 | 8.7 | 12.0 | 38.1 | 49.8 | 61.9 | 7.5 | 63.1 | 109.1 |
| | N | 251.0 | 68.0 | 72.7 | 77.2 | 9.2 | 12.6 | 38.8 | 49.8 | 63.0 | 8.0 | 64.0 | 84.5 |
| P90-4 × OH43aeae | N | 209.3 | 66.9 | 71.5 | 76.3 | 9.4 | 11.2 | 39.3 | 50.5 | 62.6 | 8.2 | 73.4 | 102.7 |
| | N | 285.2 | 66.0 | 72.7 | 77.1 | 11.1 | 12.5 | 40.4 | 52.1 | 62.3 | 7.7 | 61.5 | 105.9 |
| | SS | 176.5 | 68.1 (55.6) | 87.3 | 103.0 | 34.9 | 10.3 | 44.3 | 91.0 | 103.7 | 13.3 | 100.0 | 103.7 |
| | SS | 213.9 | 68.8 | 88.2 | 102.5 | 33.7 | 9.0 | 78.8 | 93.1 | 101.2 | 4.5 | 61.4 | 110.2 |
| P90-8 × OH43aeae | N | 129.0 | 68.7 | 72.3 | 76.3 | 7.6 | 12.8 | 40.6 | 52.3 | 62.4 | 7.9 | 61.8 | 51.3 |
| | N | 108.7 | 70.1 | 73.3 | 77.2 | 7.1 | 13.3 | 41.7 | 52.8 | 63.2 | 9.2 | 64.0 | 89.8 |
| | S | 90.8 | 67.2 (53.2) | 73.7 | 82.7 | 15.5 | 11.5 | 44.0 | 53.7 | 62.2 | 1.6 | 13.9 | 44.9 |
| | | | | | | | | | | | | | 50.3 |
| P91-15 × OH43aeae | N | 142.3 | 68.7 | 73.5 | 78.4 | 9.7 | 8.5 | 43.8 | 54.5 | 63.7 | 5.2 | 60.5 | 90.9 |
| | N | 139.7 | 68.8 | 73.4 | 78.1 | 9.3 | 9.6 | 39.8 | 53.8 | 63.5 | 3.5 | 37.1 | 46.0 |
| | N | 153.5 | 68.2 | 74.1 | 81.0 | 12.8 | 8.8 | 42.5 | 57.4 | 68.0 | 3.2 | 35.8 | 93.0 |
| | N | 173.0 | 68.7 | 73.3 | 78.0 | 9.3 | 9.2 | 42.5 | 54.4 | 64.9 | 4.2 | 45.8 | 26.7 |
| LSD$_{0.05}$ | | | .9 | .5 | 1.2 | 1.4 | 1.4 | 2.3 | 1.2 | 1.3 | 1.4 | 7.4 | 11.8 |
| LSD$_{0.01}$ | | | 1.2 | .7 | 1.6 | 1.9 | 1.9 | 3.0 | 1.6 | 1.7 | 1.9 | 9.8 | 15.0 |

[a]Crosses are shown as female × male. Hill untran. control, tissue-culture derived untransformed control in Hill background; OH43, OH43 inbred; OH43aeae, aeae mutant in OH43 background.
[b]N normal; SS, slightly shrunken; S, shrunken.
[c]$T_o$, onset temperature; $T_p$, peak temperature; $T_c$, completion temperature; ΔH, enthalpy change. Range is $T_c$–$T_o$. Thermal transition initiation temperatures are in parenthesis.
[d]% R, percentage of retrogradation. Values of starch gelatinization and retrogradation are averages of three replicates.
[e]Specific activities of BE for crosses to OH43 are presented as percentage of the mean value of (Hill untran. control × OH43); and the specific activities for crosses of OH43aeae are shown as percentage of the mean value of (Hill untran. control × OH43aeae). Values are averages of two replicates.

Flipse E, Huisman J G, Vries B J D, Bergervoet J E M, Jacobsen E, Visser R G F. (1994) Expression of a wild-type GBSS gene introduced into an amylose-free potato mutant by *Agrobacterium tumefaciens* and the inheritance of the inserts at the microsporic level. Theor Appl Genet. 88:369–375.

Fromm M. (1994) Production of transgenic maize plants via microprojectile-mediated gene transfer, pp. 677–684. In M. Freeling and V Walbot (Eds.), The Maize Handbook, Springer-Verlag Inc., New York, N.Y.

James, M. G., Robertson, D. S. & Myers, A. M. (1995) Characterization of the maize gene sugary1, a determinant of starch composition in kernels. Plant Cell 7, 417–429.

Jane J, Chen Y, Lee L, McPherson A, Wong K, Radosavljevic, Kasemsuwan T. (1999) Effects of amylopectin branch chain length and amylose content on the gelatinization and pasting properties of starch. Cereal Chem. 76(5): 629–637.

Jobling S A, Schwall G P, Westcott R J, Sidebottom C M, Debet M, Gidley M J, Jeffcoat R, Safford R. (1999) A minor form of starch branching enzyme in potato (*Solanum tuberosum* L.) tubers has a major effect on starch structure: cloning and characterization of multiple forms of SBE A. Plant J 18(2):163–171.

Johnson L A, Baumel C P, Hardy C L, White P J. (1999a) Identifying valuable corn quality traits for starch production. Iowa State University Extension Publication DEC 194.

Johnson L A, Hardy C L, Baumel C P, Yu T, Sell J L. (1999b) Identifying valuable corn quality traits for livestock feed. Iowa State University Extension Publication DEC 195.

Kasemsuwan T, Jane J, Schnable P, Stinard P, Robertson D. (1995) Characterization of the dominant mutant amylose-extender (Ae1-5180) maize starch. Cereal Chem. 72(5): 457–464.

Kortstee A J, Vermeesch A M S, Vries B J D, Jacobsen E, Visser R G F (1996) Expression of *Escherichia coli* branching enzyme in tubers of amylose-free transgenic potato leads to an increased branching degree of the amylopectin. Plant J 10(1):83–90.

Lloyd J R, Landschutze V, Kossmann J. (1999) Simultaneous antisense inhibition of two starch-synthase isoforms in potato tubers leads to accumulation of grossly modified amylopectin. Biochem J. 338:515–521.

Martin C, Smith A M. (1995) Starch biosynthesis. Plant Cell. 7:971–985.

Matzke M A, Matzke A J M, Eggleston W B. (1996) Paramutation and transgene silencing: a common response to invasive DNA? Trends Plant Sci. 1(11): 382–388.

Matzke M A, Matzke A J M. (1998) Epigenetic silencing of plant transgenes as a consequence of diverse cellular defence responses. Cell Mol Life Sci. 54:94–103.

Myers A M, Morell M K, James M G, Ball S G. (2000) Recent progress toward understanding biosynthesis of the amylopectin crystal. Plant Physiol. 122: 989–997.

Reina, M, Ponte, I, Guillen, P, Boronat, A, and Palau, J. (1990) Sequence analysis of a genomic clone encoding a Zc2 protein from *Zea mays* W64 A. Nucleic Acids Res. 18(21): 6426.

Safford R, Jobling S A, Sidebottom C M, Westcott R J, Cooke D, Tober K J, Strongitharm B H, Russell A, Gidley M J. (1998) Consequences of antisense RNA inhibition of starch branching enzyme activity on properties of potato starch. Carbohydrate Polymers 35: 155–168.

Schwall G P, Safford R, Westcott R J, Jeffcoat R, Tayal A, Shi Y C, Gidley M J, Jobling S A. (20000) Production of very-high-amylose potato starch by inhibition of SBE A and B. Nat Biotechnol. 18(5):551–554.

Shi Y C, Seib P A. (1992) The structure of four waxy starches related to gelatinization and retrogradation. Carbohydr Res. 227:131–145.

Shi Y C, Seib P A. (1995) Fine structure of maize starches from four wx-containing genotypes of the W64A inbred line in relation to gelatinization and retrogradation. Carbohydrate Polymers. 26:141–47.

Song Y, Jane J (2000) Characterization of barley starches of waxy, normal, and high amylose varieties. Carbohydrate Polymers. 41:365–377.

Stark D M, Timmerman K P, Barry G F, Preiss J, Kishore G M. (1992) Regulation of the amount of starch in plant tissues by ADP glucose pyrophosphorylase. Science. 258: 287–292.

Steel R G D, Torrie J H. (1960) Principles and Procedures of Statistics. McGraw-Hill, New York.

Sun C, Sathish P, Ahlandsberg S, Deiber A, Jansson C. (1997) Identification of four starch branching enzymes in barley endosperm: partial purification of forms I, IIa and IIb. New Phytol. 215–222.

Sun C, Sathish P, Ahlandsberg S, Jansson C. (1998) The two genes encoding starch-branching enzymes IIa and IIb are differentially expressed in barley. Plant Physiol. 118: 37–49.

Terada R, Nakajima M, Isshiki M, Okagaki R J, Wessler S R, Shimamoto K. (2000) Antisense Waxy genes with highly active promoters effectively suppress Waxy gene expression in transgenic rice. Plant Cell Physiol. 41(7): 881–888.

Wang Y J, White P, Pollak L. (1992) Thermal and gelling properties of maize mutants from OH43 inbred line. Cereal Chem. 69(3):328–334.

Wolters A A, Visser R G. (2000) Gene silencing in potato: allelic differences and effect of ploidy. Plant Mol. Biol. 43:377–386.

Yuan R C, Thompson D B, Boyer C D. (1993) Fine structure of amylopectin in relation to gelatinization and retrogradation behavior of maize starches from three wx-containing genotypes in two inbred lines. Cereal Chem. 70:81–89.

The invention claimed is:

1. A transgenic corn plant, corn plant cell, or corn plant tissue comprising:
   a polynucleotide transgene that encodes barley starch branching enzyme (SBE) IIa comprising SEQ ID NO:2 wherein the expression of barley SBE IIa in the transgenic corn plant changes a cornstarch characteristic as compared to a plant of the same genetic background without the polynucleotide transgene.

2. The transgenic corn plant, corn plant cell, or corn plant tissue of claim 1 wherein the polynucleotide has the nucleotide sequence of nucleotide 7 to nucleotide 2208 of SEQ ID NO:1.

3. The transgenic corn plant of claim 1 wherein seeds grown on the transgenic plant contain cornstarch having at least one of the characteristics of lower gelatinization temperature, lower retrogradation rate, higher gelatinization temperature, higher retrogradation rate, or higher amylose content in comparison to cornstarch from seeds of a non-transgenic corn plant of the same genetic background and being grown under the same conditions.

4. The transgenic corn plant of claim 3, wherein seeds grown on the transgenic plant contain cornstarch having at least one of the characteristics of lower gelatinization temperature or lower retrogradation rate.

5. The transgenic corn plant of claim 3, wherein seeds grown on the transgenic plant contain cornstarch having at least one of the characteristics of higher gelatinization temperature or higher retrogradation rate.

6. A seed derived from the transgenic corn plant of claim 1 wherein the seed comprises the polynucleotide transgene.

7. The seed of claim 6 wherein the seed contains cornstarch having at least one of the characteristics of lower gelatinization temperature, lower retrogradation rate, higher gelatinization temperature, higher retrogradation rate, or higher amylose content in comparison to cornstarch from a seed of a non-transgenic corn plant.

8. The seed of claim 7 wherein the seed contains cornstarch having at least one of the characteristics of lower gelatinization temperature or lower retrogradation rate.

9. The seed of claim 7 wherein the seed contains cornstarch having at least one of the characteristics of higher gelatinization temperature or higher retrogradation rate.

10. A method for making a transgenic corn plant of claim 1 comprising the steps of:
    contacting a corn plant cell with a nucleic acid comprising a polynucleotide encoding barley SBE IIa comprising SEQ ID NO:2;
    identifying a plant cell carrying the polynucleotide;
    regenerating a transgenic plant from the plant cell carrying the polynucleotide; and
    determining whether seeds from the transgenic plant contain cornstarch having at least one characteristic changed in comparison to cornstarch from seeds of a non-transgenic corn plant of the same genetic background and being grown under the same conditions.

11. A method for making a transgenic corn plant of claim 1 comprising the steps of:
    randomly inserting a nucleic acid comprising a polynucleotide encoding barley SBE IIa comprising SEQ ID NO:2 into the genome of a corn plant; and
    selecting plants having seeds that contain cornstarch having at least one characteristic changed in comparison to cornstarch from seeds of a non-transgenic corn plant of the same genetic background and being grown under the same conditions.

12. The method of claim 10 or claim 11, wherein the polynucleotide has a nucleotide sequence of nucleotide 7 to nucleotide 2208 of SEQ ID NO:1.

13. The method of claim 10 or claim 11, wherein the changed characteristic of cornstarch is gelatinization temperature, retrogradation rate, or amylose content.

14. The method of claim 10 or claim 11, wherein the cornstarch with a changed characteristic has a lower gelatinization temperature, lower retrogradation rate or both.

15. The method of claim 10 or claim 11, wherein the cornstarch with a changed characteristic has a higher gelatinization temperature, higher retrogradation rate or both.

* * * * *